US008235588B2

(12) United States Patent
Louban et al.

(10) Patent No.: US 8,235,588 B2
(45) Date of Patent: Aug. 7, 2012

(54) METHOD FOR AUTOMATED TESTING OF A MATERIAL JOINT

(75) Inventors: Roman Louban, Crailsheim (DE);
Juergen Zettner, Veitsbronn (DE);
Christoph Doettinger, Erlangen (DE)

(73) Assignee: Thermosensorik GmbH, Erlangen (DE)

( * ) Notice: Subject to any disclaimer, the term of this patent is extended or adjusted under 35 U.S.C. 154(b) by 512 days.

(21) Appl. No.: 12/520,504

(22) PCT Filed: Dec. 11, 2007

(86) PCT No.: PCT/EP2007/010800
§ 371 (c)(1),
(2), (4) Date: Jun. 19, 2009

(87) PCT Pub. No.: WO2008/077479
PCT Pub. Date: Jul. 3, 2008

(65) Prior Publication Data
US 2010/0091812 A1    Apr. 15, 2010

(30) Foreign Application Priority Data

Dec. 21, 2006   (DE) .................. 10 2006 061 794

(51) Int. Cl.
*G01N 25/72* (2006.01)
*G01N 21/88* (2006.01)
*G01J 5/02* (2006.01)
(52) U.S. Cl. .............. 374/4; 374/30; 374/137; 374/121; 374/57; 250/338.1; 250/341.6

(58) Field of Classification Search ................ 374/4, 16, 374/26, 7, 43, 44, 45, 57, 120, 121, 129, 374/141, 29, 30, 137, 102, 103, 107, 110, 374/111, 112, 115, 1, 2, 134, 139, 5; 250/338.1, 250/340, 341.1, 341.2, 341.6; 340/588, 589; 219/617, 602, 121.13, 121.16, 121.17, 121.45, 219/121.65; 356/237.1
See application file for complete search history.

(56) References Cited

U.S. PATENT DOCUMENTS 4,611,111 A * 9/1986 Baheti et al. ............. 219/124.34
(Continued)

FOREIGN PATENT DOCUMENTS

DE    10150633 A1    4/2003
(Continued)

OTHER PUBLICATIONS

Maldague, X.P.V. et al.: Theory and Practice of Infrared Technology for Nondestructive Testing. John Wiley & Sons, May 2001.
(Continued)

*Primary Examiner* — Gail Verbitsky
(74) *Attorney, Agent, or Firm* — Nixon Peabody LLP; Joseph Bach, Esq.

(57) ABSTRACT

In a method for automated, contactless and non-destructive testing of a material joint (4), a dynamic threshold value is varied between a minimum threshold value and a maximum threshold value, with regions of a heat flow dynamics through the material joint (4) being determined which represent values of the heat flow dynamics exceeding the dynamic threshold value. The regions of the heat flow dynamics are examined with respect to an abrupt change in perimeter. An Abrupt change in perimeter occurs if a boundary (7) between a molten zone (5) and a non-molten but still adhering zone (6) of the material joint (4) is being crossed.

10 Claims, 4 Drawing Sheets

U.S. PATENT DOCUMENTS

| | | | |
|---|---|---|---|
| 4,792,683 A | | 12/1988 | Chang et al. |
| 4,877,940 A | * | 10/1989 | Bangs et al. ............. 219/124.34 |
| 5,250,809 A | * | 10/1993 | Nakata et al. ................. 250/330 |
| 5,292,195 A | | 3/1994 | Crisman, Jr. |
| 5,721,415 A | | 2/1998 | Fortmann et al. |
| 5,775,806 A | * | 7/1998 | Allred ........................... 374/124 |
| 6,153,848 A | * | 11/2000 | Nagae et al. ................. 219/110 |
| 6,585,146 B2 | * | 7/2003 | Shepard ........................ 228/104 |
| 6,940,037 B1 | * | 9/2005 | Kovacevic et al. ....... 219/121.64 |
| 7,044,634 B2 | * | 5/2006 | Sandvoss ........................... 374/5 |
| 7,083,327 B1 | * | 8/2006 | Shepard ........................... 374/46 |
| 7,425,093 B2 | * | 9/2008 | Wickersham et al. ............ 374/5 |
| 7,909,505 B2 | * | 3/2011 | Alexandrov et al. ........... 374/10 |
| 2005/0043891 A1 | * | 2/2005 | Bush ................................ 702/13 |
| 2010/0086003 A1 | * | 4/2010 | Pfitzner et al. .................... 374/5 |
| 2010/0288734 A1 | * | 11/2010 | Dave et al. .................... 219/73.2 |
| 2011/0240607 A1 | * | 10/2011 | Stecker et al. ........... 219/121.17 |
| 2011/0310923 A1 | * | 12/2011 | Strohmeyer ....................... 374/4 |

FOREIGN PATENT DOCUMENTS

| | | |
|---|---|---|
| JP | 08122051 A | 5/1996 |
| WO | 99/10733 A1 | 3/1999 |
| WO | 0150116 A1 | 7/2001 |

OTHER PUBLICATIONS

Demant, Ch. et al.: Industrielle Bildverarbeitung: wie optische Qualitäts-kontrolle wirklich funktioniert. Springer, Berlin, Heidelberg, 1998.

Gerthsen Physik, 23rd edition, p. 130 ff., Springer Verlag, 2006.

* cited by examiner

METHOD FOR AUTOMATED TESTING OF A MATERIAL JOINT

The invention relates to a method for automated, contactless and non-destructive testing of a material joint of at least two mating parts according to the preamble of claim 1.

Weld points are important material joints for industrial applications. A weld point usually comprises a two-section joint which consists of a molten and a non-molten zone. The molten zone is located in an inner region of the weld point, thus forming the so-called weld nugget. The non-molten zone surrounds the weld nugget and is referred to as weld glue. In the non-molten zone, the mating parts are not welded together. The strength of the joint between the mating parts is therefore not sufficient in the non-molten zone as there is only a certain amount of adherence. The quality of the weld point is therefore substantially determined by the weld nugget.

It is known to evaluate the quality of a weld point by means of destructive testing or examination. An examination of this type can however only be performed by random sampling. A more frequent examination—up to an examination of 100 percent of all samples—is only performable by means of non-destructive examination.

Heat flow thermography is a long-established contactless and non-destructive examination method. According to this method, a test sample is excited by at least one excitation source in order to generate a heat flow. The thermal radiation emitted by the test sample is recorded in a sequence of images by means of at least one infrared sensor. In a computing unit, the recorded sequence of images is developed into result images of various types. Result images of these types are for instance an amplitude image and a phase image which respectively illustrate the amplitude and the travel time of the thermal waves at various points of a material joint. By means of a phase image, local differences in heat conductivity of a material joint can be made visible (Theory and Practice of Infrared Technology for Nondestructive Testing, Xavier P. V. Maldague, John Wiley and Sons, Inc., 2001).

A method for automated testing of weld points is disclosed in WO 01/50116 A1 where the quality of a weld point is evaluated by means of a half-value period of the heat flow. A low half-value period of the heat flow at the individual image points indicates a good-quality weld joint. The disadvantage of this method is that the absolute half-value periods that are detected do not provide any objective information as to the location of the boundary between the weld nugget and the weld glue. With this method, an automated determination of the size and position of the weld point is therefore impossible on an industrial scale.

DE 101 50 633 A1 discloses a method for automated testing of a weld point where the quality of the weld point is evaluated by means of a phase image. The phase image that is used is obtained by means of given parameters which are defined before the sequence of images to be examined is taken. The quality of the weld joint is determined by means of clearly defined threshold values. The disadvantage of this method is that the weld nugget to be evaluated is not reliably detectable on an industrial scale by means of clearly defined threshold values.

It is the object of the invention to provide a method for automated, contactless and non-destructive testing of a material joint which allows the molten zone of a material joint to be reliably detected and evaluated.

This object is achieved by the features of claim 1. It has been found according to the invention that the boundary between the molten zone and the non-molten but still adhering zone is an additional obstacle for the heat flow. This boundary causes an abrupt decrease of the heat flow dynamics. Immediately behind this boundary, the dynamics of the heat flow in the non-molten zone increases again. In a result image in which the heat flow dynamics through the material joint is illustrated as intensity values of the result image, this is shown by an intensity bead which forms at this point.

In a first step, this result image is used to determine a heat flow dynamics of surroundings of the material joint to be examined, said heat flow dynamics thus forming an image background. The heat flow dynamics of the image background is for instance determined by means of a histogram. A value which is lifted from the heat flow dynamics of the image background is defined as a minimum dynamic threshold value which defines a region where both the non-molten zone as well as the molten zone of the material joint may be located. In a next step, a peak value of the heat flow dynamics through the material joint is determined in this region, the peak value being a maximum dynamic threshold value. A dynamic threshold value that is varied between the minimum threshold value and the maximum threshold value defines a sequence of regions on the result image, with each of these regions representing the values of the heat flow dynamics through the material joint that exceed the dynamic threshold value. These regions are examined with respect to their perimeter. The intensity bead causes the outer shape of these regions to increase abruptly when crossing the boundary between the molten zone and the non-molten zone. The perimeter of these regions is measured and represented by a feature vector, the perimeter being a numerical illustration of the outer shape of said regions. An abrupt increase in this feature vector indicates that the associated region has enclosed a portion of the non-molten zone. This abrupt increase of the feature vector may for instance be detected by means of conventional methods such as curve smoothing and curve examination. The boundary between the molten zone and the non-molten zone of a material joint can thus be localized dynamically and objectively. In this way the molten zone is reliably detectable. The detected molten zone is then evaluated in terms of its position and size.

If excitation and detection of the heat flow occur on the same side of the material joint, the heat flow dynamics through the material joint is reduced when crossing the boundary between the molten zone and the non-molten zone. In this case, the intensity bead causes the perimeter of the examined regions to decrease abruptly when crossing the boundary, with the result that an abrupt decrease can be observed in the feature vector.

The described method is generally identical for all mating parts. Thus material joints of mating parts from identical or different materials can be examined. Furthermore, the method allows one to examine weld joints as well as solder joints. These material joints show a boundary between a welded and a non-welded zone or a boundary between a soldered and a non-soldered zone, respectively. Accordingly, an intensity bead develops on the result image which illustrates local differences in heat conductivity of the material joint to be examined. Said intensity bead can be detected by means of conventional signal and image processing methods in order to detect and evaluate the weld and solder joint.

Excitation of the material joint and detection of the heat flow may generally occur on different sides or on identical sides of the material joint. Accordingly, result images of various types are evaluated, which illustrate a time and space resolved heat flow in transmission and/or reflection. It must be ensured that the measurement results of the heat flow are not considerably influenced by intensity variations of the excitation source, the state and properties of the material surface and the material thickness of the mating parts. Therefore, a result image is used which does not illustrate absolute values of the heat flow or of its speed through the material joint to be examined but local speed differences of the heat flow. A result image of this type may for instance be a phase image which is obtained using infrared lock-in thermography. (Theory and Practice of Infrared Technology for Nondestructive Testing, Xavier P. V. Maldague, John Wiley and Sons, Inc., 2001). A phase image illustrates the travel time of the thermal waves when propagating through the material joint, with the result that differences in heat conductivity of the material joint occurring between the various image points of the result image become visible. The local speed differences of the heat flow are referred to as heat flow dynamics.

A reference region according to claim 2 ensures that the minimum threshold value is obtained from the heat flow dynamics of the image background.

The maximum threshold value is easily detectable by means of a test region according to claim 3. The test region may for instance be located in the center of the region to be examined. The size of the test region can be determined experimentally, wherein Shannon's sampling theorem needs to be observed (Industrial Image Processing, Christian Demant, Bernd Streicher-Abel, Peter Waszkewitz, Springer-Verlag, 1998). The size of the test region may for instance be defined to be 3×3 pixels.

Determining the maximum threshold value by means of several test regions of the same size according to claim 4 is reliable. The test regions are generated in such a way that a test region with a defined size is displaced in the region which represents the values of the heat flow dynamics that exceed the minimum threshold value. The size of the test regions may for instance be defined to be 3×3 pixels.

Determining the increment size by means of an iterative process according to claim 5 allows one to find an optimum increment size. In order to determine an optimum increment size, it is for instance conceivable to start with an increment size of 1.

A weld point according to claim 6 which comprises a molten zone referred to as weld nugget and a non-molten but still adhering zone referred to as weld glue is an important material joint for industrial applications; the advantages of the method according to the invention are therefore particularly evident.

A material characteristic curve according to claim 7 allows one to exactly determine the remaining material thickness of a weld point and therefore of the indentation at the weld point that was formed by the welding gun. In order to examine the material joint, the material characteristic curve for the material combination of the mating parts to be examined needs to be generated in advance. The material characteristic curve illustrates a nonlinear dependence of the peak value of the heat flow dynamics from the remaining material thickness of a weld point. The data required for this characteristic curve are obtained at various reference weld points of the same material combination, the reference weld points having different remaining material thicknesses. The transmitted component and the dissipated component of the heat flow play different roles in the determination of the remaining material thickness. If the remaining material thickness of a weld point is small, it is the transmitted component of the heat flow that determines the peak value of the heat flow dynamics. In the case of a greater remaining material thickness, it is the dissipated component of the heat flow which is more important. The peak value measured in the region of the weld nugget can therefore be used to determine the remaining material thickness. The peak value of the heat flow dynamics corresponds to the maximum threshold value which is measured in the region of the weld nugget of the weld point. The remaining material thicknesses of the reference weld points are measured using an independent method.

A comparison with a first limiting value according to claim 8 allows one to detect holes. If the value of the heat flow dynamics is too high, this indicates the presence of a hole in the weld point. The first limiting value is determined empirically.

A comparison with a second limiting value according to claim 9 allows one to detect cavities. If the value of the heat flow dynamics is too low, this indicates the presence of a cavity in the weld nugget. A weld nugget of this type is referred to as a burned out weld nugget. The second limiting value is determined empirically.

A development of the method according to claim 10 allows one to specifically search for surface damages in the region of the detected weld nugget. The detection of damages is restricted to the region of the weld nugget so that the method is protected from producing false results. The further image may for instance be one of the recorded thermal images or a further result image. The result image may for instance be an amplitude image which is obtained using infrared lock-in thermography. The amplitude image shows the amplitude of the thermal waves when propagating through the weld point. Depending on the origin, size and position as well as the combination of the detected defects, the quality of the weld point can be precisely classified and evaluated. Furthermore, it is possible to identify and trace the causes of the damaged weld point, thus allowing a statistical evaluation of the entire welding process to be performed which may serve as a basis for quality assurance.

Further features and advantages of the invention will become apparent from the description of an embodiment by means of the drawing in which.

Figure 1:
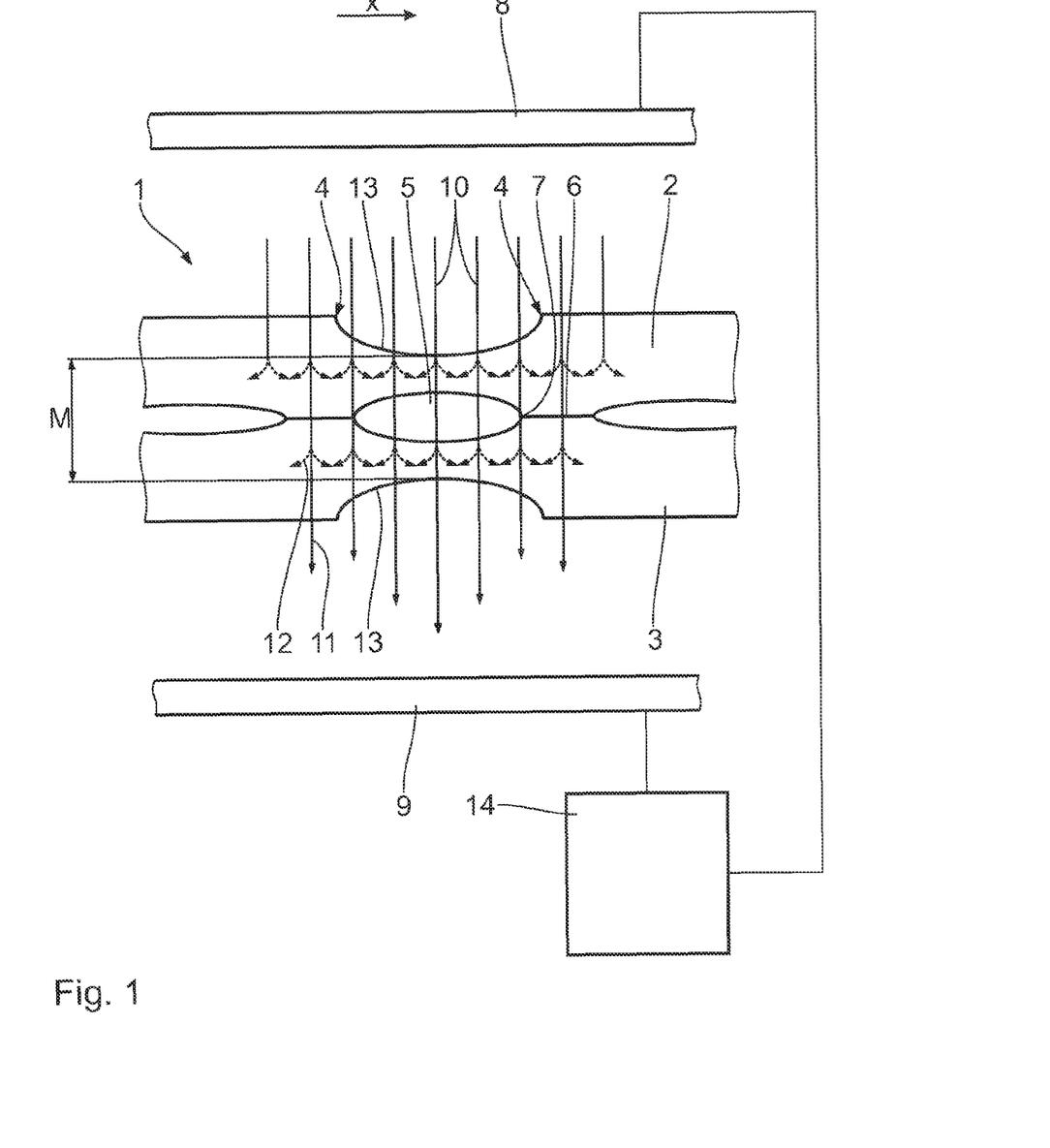
FIG. 1 shows a section through a material joint in the form of a weld point.

A test sample 1 comprises a first mating part 2 and a second mating part 3 which are interconnected by a material joint 4. The mating parts 2, 3 may be formed of identical or different materials having identical or different material thicknesses. The material joint 4 is a weld point. The following is a description of the material joint in the form of a weld point 4.

The weld point 4 forms a two-section joint which consists of a molten zone 5 and a non-molten zone 6 surrounding said molten zone 5. Between the molten zone 5 and the non-molten zone 6, there is a boundary 7 which delimits the molten zone 5 and separates it from the non-molten but still adhering zone 6. The molten zone is hereinafter referred to as weld nugget 5 while the non-molten zone is referred to as weld glue 6. An excitation source 8 and an infrared sensor 9 are arranged on opposite sides of the test sample 1.

The test sample 1 and the weld point 4 to be examined are excited in pulses by means of the excitation source 8. A heat flow 10 is generated which consists of a transmitted component 11 and a dissipated component 12. The dissipated component 12 is also referred to as dissipative component. The transmitted component 11 of the heat flow 10 is recorded by means of the infrared sensor 9 in a sequence of thermal images taken one after the other.

Each of the mating parts 2, 3 of the weld point 4 has an indentation 13. The indentations 13 are formed by a welding gun which is used for producing the weld point 4. The indentations 13 define a remaining material thickness M.

A computing unit 14 is provided for evaluation of the recorded sequence of thermal images, the computing unit 14 being connected to the excitation source 8 and the infrared sensor 9. The sequence of thermal images is developed into result images of various types. A result image in the form of a phase image illustrates the heat flow dynamics W through the weld point 4. The heat flow dynamics W describes the local speed differences of the heat flow 10 when propagating through the weld point 4, and therefore the local differences in heat conductivity.

Figure 2:
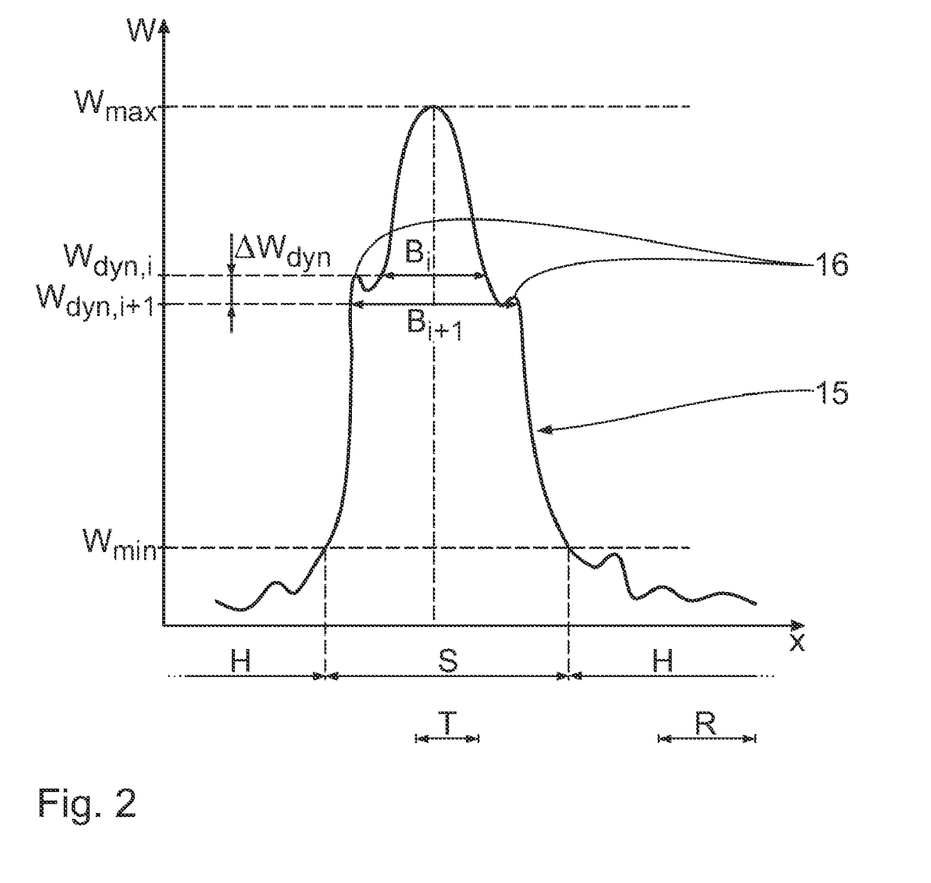
FIG. 2 is a view of a one-dimensional distribution of a heat flow dynamics through the weld point.

FIG. 2 shows a one-dimensional distribution 15 of the heat flow dynamics W along a cross-section coordinate x. The heat flow dynamics W generally shows a two-dimensional distribution. From a qualitative point of view, said two-dimensional distribution corresponds to the one-dimensional distribution 15, the two-dimensional distribution may however have a non-symmetric and irregular shape corresponding to the geometry of the weld point 4.

The two-dimensional distribution of the heat flow dynamics W is substantially determined by the geometry of the weld point 4. The geometry of the weld point 4 is impressed by the indentations 13 of the weld gun. The following is a more detailed description of the one-dimensional distribution 15 of the heat flow dynamics W. In order to be able to correctly detect the weld nugget, however, it is the two-dimensional distribution of the heat flow dynamics W that needs to be evaluated; the following descriptions therefore apply correspondingly to the two-dimensional distribution.

In a center of the weld point 4, the heat flow dynamics W has a peak value, with the heat flow dynamics W decreasing from this peak value towards the periphery of the weld point 4. It has been found according to the invention that the boundary 7 between the weld nugget 5 and the weld glue 6 leads to an additional local decrease of the heat flow dynamics W, with the heat flow dynamics W increasing again immediately behind this boundary 7. This effect results in an intensity bead 16 which is shown in FIG. 2 for the one-dimensional distribution 15 of the heat flow dynamics W. The effect of the formation of an intensity bead 16 around the weld nugget 5 may be non-symmetric and irregular; it is therefore the two-dimensional distribution of the heat flow dynamics W that needs to be evaluated in order to correctly detect the weld nugget 5.

In order to detect the weld nugget 5, a minimum threshold value $W_{min}$ is determined in a first step. The minimum threshold value $W_{min}$ exceeds the heat flow dynamics W of an image background H. The minimum threshold value $W_{min}$ is obtained from a reference region R of the heat flow dynamics W of the image background H, the reference region R forming a part of the image background H.

Furthermore, a maximum threshold value $W_{max}$ is determined which corresponds to the peak value of the heat flow dynamics W through the weld point 4. The maximum peak value $W_{max}$ is obtained from a test region T which is located in the center of a region S which represents the values of the heat flow dynamics W exceeding the minimum threshold value $W_{min}$. The maximum threshold value $W_{max}$ is an average value of the values of the heat flow dynamics W obtained from the test region T.

Alternatively, the maximum threshold value $W_{max}$ may be obtained from several test regions T of the same size which are offset relative to each other in the region S, with an average value of the values of the heat flow dynamics W being obtained from the test region T for each of the test regions T. The maximum threshold value $W_{max}$ is the maximum value of these average values.

In order to detect the weld nugget 5, a dynamic threshold value $W_{dyn}$ is varied between the minimum threshold value $W_{min}$ and the maximum threshold value $W_{max}$. The varied dynamic threshold values are referred to as $W_{dyn,i}$, with i=1 to n. The dynamic threshold value $W_{dyn}$ is varied with an increment size $\Delta W_{dyn}$. This means that two subsequent dynamic threshold values $W_{dyn,i}$ and $W_{dyn, i+1}$ are spaced from each other by the increment size $\Delta W_{dyn}$. The optimum increment size $\Delta W_{dyn}$ can be obtained iteratively.

An associated region $B_i$ of the heat flow dynamics W through the weld point 4 is determined for each dynamic threshold value $W_{dyn, i}$, with the region $B_i$ representing the values of the heat flow dynamics W exceeding the dynamic threshold value $W_{dyn, i}$. Each region $B_i$ has an associated perimeter $U_i$ which is determined and represented by a feature vector. All regions B are then examined with respect to an abrupt change in perimeter $\Delta U$. If the dynamic threshold value $W_{dyn}$ is varied between the maximum threshold value $W_{max}$ and the minimum threshold value $W_{min}$, an abrupt increase of the perimeter U occurs if a region B to be examined crosses the boundary 7 between the weld nugget 5 and the weld glue 6. FIG. 2 shows a region $B_i$ with a perimeter $U_i$ when the region $B_i$ has not yet crossed the boundary 7. FIG. 2 further shows a region $B_{i+1}$ with a perimeter $U_{i+1}$ where the region $B_{i+1}$ has already crossed the boundary 7. The region $B_{i+1}$ thus encloses a portion of the weld glue 6. The enclosed portion of the weld glue 6 shows a greater heat flow dynamics W than the boundary 7. The region $B_i$ is thus the greatest region which has not yet crossed the boundary 7 and does therefore not enclose a portion of the weld glue 6. The region $B_i$ therefore substantially corresponds to the weld nugget 5. The position and the size of the weld nugget 5 can therefore be evaluated by means of the region $B_i$ and its associated perimeter $U_i$.

Figure 3:
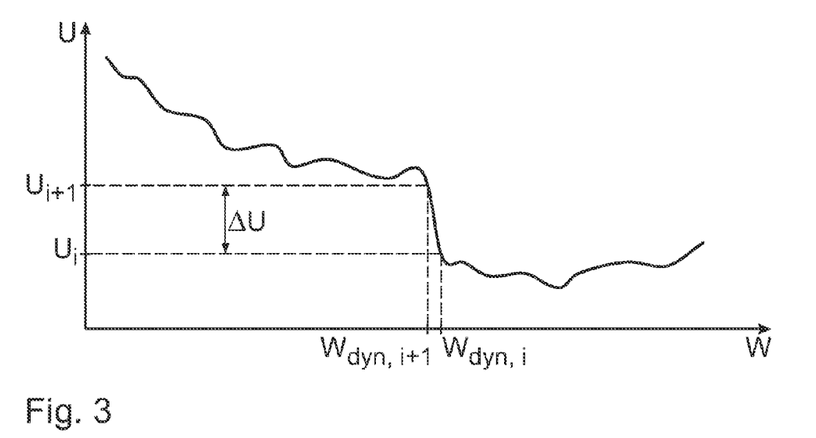
FIG. 3 is a view of a first feature vector by means of which a perimeter of regions to be examined is represented as a function of the heat flow dynamics.
Figure 4:
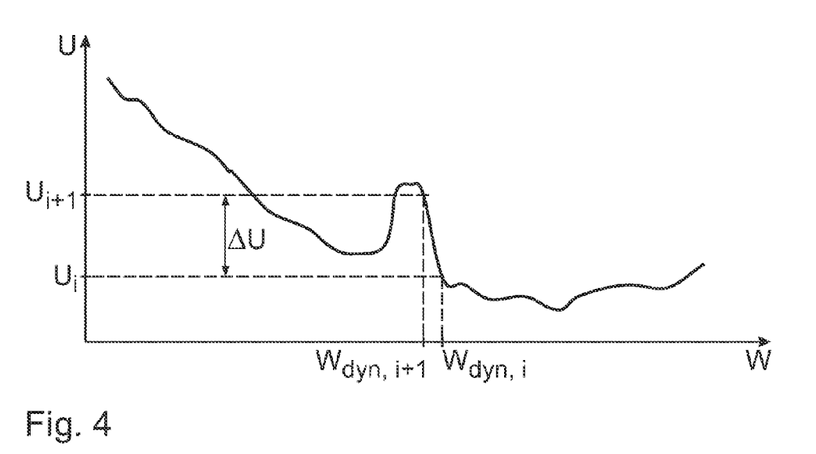
FIG. 4 is a view of a second feature vector by means of which a perimeter of regions to be examined is represented as a function of the heat flow dynamics.

Depending on the state of the outer shape of the regions B to be examined, the abrupt change in perimeter $\Delta U$ may be followed by a rapid decrease in perimeter as shown in FIG. 4, or by another increase of the perimeter U as shown in FIG. 3. This is the result of the Poisson effect (Gerthsen Physik, $23^{rd}$ edition, p. 130 ff., Springer Verlag, 2006) which states that an object with a distinct outer shape tends to either eliminate or further increase the deviation of its shape from an ideal circle when the surface area of said object increases. If these deviations are eliminated when the size of the object increases, this will result in a reduction of the perimeter. As soon as the deviations are substantially eliminated, the perimeter of the object will increase continuously again.

The abrupt change in perimeter $\Delta U$ of the regions B to be examined is detectable by means of conventional signal and image processing methods. They allow a non-symmetric and irregular formation of the intensity bead 16 around the weld nugget 5 to be detected. A dynamic and adaptive and therefore automated detection of the weld nugget 5 is thus guaranteed.

Figure 5:
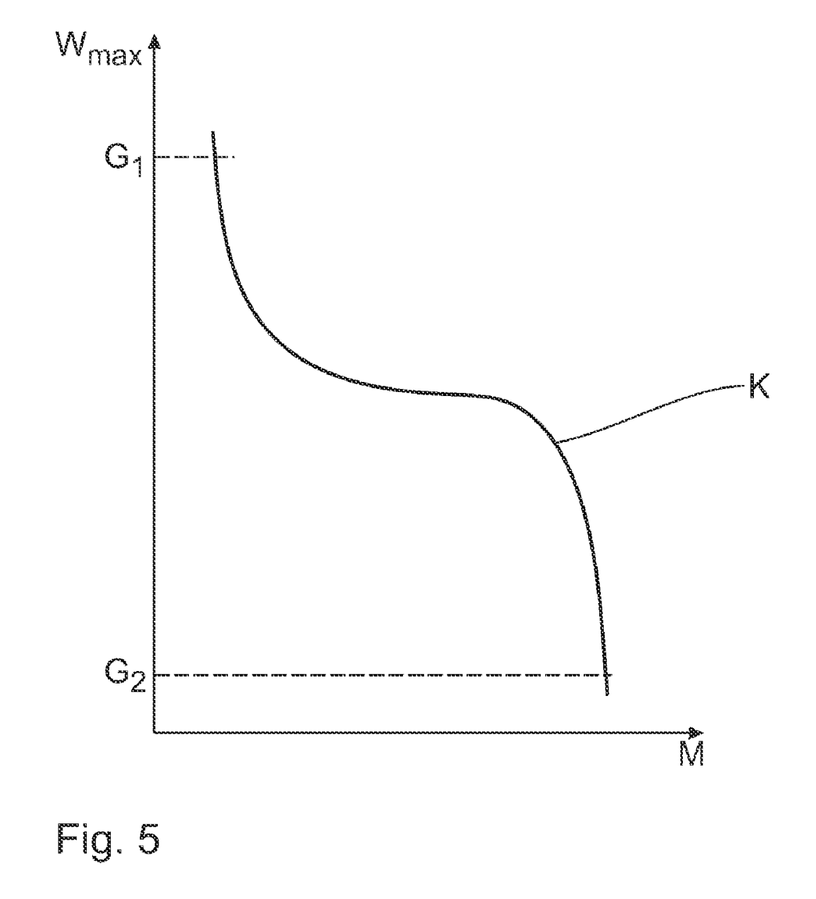
FIG. 5 is a material characteristic curve which represents a peak value of the heat flow dynamics as a function of a remaining material thickness.

The peak value of the heat flow dynamics W, which is the maximum threshold value $W_{max}$, allows a contactless and non-destructive examination of the remaining material thickness M of the weld point 4 to be performed. In order to determine the remaining material thickness M, a material characteristic curve K is generated in advance with respect to the material combination of the mating parts 2, 3 to be examined. The characteristic curve K is determined by means of reference weld points which have different remaining material thicknesses, the reference weld points interconnecting corresponding mating parts 2, 3 which are to be examined later. For each reference weld point, a remaining material thickness M is measured by means of an independent method. Furthermore, a peak value of the heat flow dynamics W is measured for each reference weld point. The characteristic curve K describes the nonlinear dependence of the peak value of the heat flow dynamics W from the remaining material thickness M.

The characteristic curve K allows one to examine the remaining material thickness M of the weld point 4 to be examined and of the indentations 13 at the weld point 4 that were formed by the weld gun. The maximum peak value $W_{max}$ of the weld point 4 to be examined is compared with a first limiting value $G_1$; if this limiting value $G_1$ is exceeded, this indicates the presence of a hole in the weld point 4. Furthermore, the maximum peak value $W_{max}$ of the weld point 4 to be examined is compared with a second limiting value $G_2$; if said maximum peak value $W_{max}$ is less than this limiting value $G_2$, this indicates the presence of a cavity in the weld point 4. The limiting values $G_1$, $G_2$ are determined empirically.

Furthermore, the method allows various surface damages of the weld point 4 to be detected and evaluated. Detection and evaluation of surface damages takes place in the detected region $B_i$ of the weld nugget 5. Surface damages are detected by means of another image which is provided with a coordinate system that is identical to that of the result image used to detect the weld nugget 5. An image of this type may for instance be a thermal image or an amplitude image which is generated by means of infrared lock-in thermography (Theory and Practice of Infrared Technology for Nondestructive Testing, Xavier P. V. Maldague, John Wiley and Sons, Inc., 2001). The detection of defects occurs exclusively in the region $B_i$ of the weld nugget 5 so that false results are avoided. The boundary 7 between the weld nugget 5 and the weld glue 6 is for instance not identified as a defect. The evaluation and detection of defects may for instance be performed using conventional signal and image processing methods. The weld point 4 can be classified depending on the origin, size and position as well as the combination of the detected weld point defects. This allows one to precisely evaluate the quality of the weld point 4.

The method according to the invention enables an automated, contactless and non-destructive examination of a weld point 4 to be performed on an industrial scale. The method provides for a comprehensive detection of defects which ensures a precise and reliable classification of the weld point 4 to be examined.

The invention claimed is:

1. A method for automated, contactless and non-destructive testing of a material joint (4) of at least two mating parts (2, 3),
   a. with the material joint (4) being a two-section joint which consists of
      i. a molten zone (5) and
      ii. a non-molten zone (6) surrounding said molten zone (5);
   b. with an examination of infrared images taking place in such a way that
      i. at least one excitation source (8) excites a test sample (1);
      ii. at least one infrared sensor (9) detects a developing heat flow in a sequence of thermal images;
      iii. result images are obtained from the sequence of thermal images; and
      iv. the thermal images and the result images are examined;
   wherein
   c. the molten zone (5) is detected from a result image, which illustrates a heat flow dynamics (W) through the material joint (4), in such a way that
      i. a minimum threshold value ($W_{min}$) is determined which exceeds a heat flow dynamics (W) of an image background (H);
      ii. a maximum threshold value ($W_{max}$) is determined which corresponds to a peak value of the heat flow dynamics (W) through the material joint (4);
      iii. a dynamic threshold value ($W_{dyn}$) is varied between the minimum threshold value ($W_{min}$) and the maximum threshold value ($W_{max}$);
      iv. a sequence of regions (B) of the heat flow dynamics (W) through the material joint (4) is determined which represent the values of the heat flow dynamics (W) exceeding the dynamic threshold value ($W_{dyn}$);
      v. the regions (B) of the heat flow dynamics (W) are examined with respect to an abrupt change in perimeter ($\Delta U$);
      vi. the molten zone (5) is determined as a region ($B_i$) from the regions (B), the abrupt change in perimeter ($\Delta U$) indicating that a boundary (7) between the molten zone (5) and the non-molten zone (6) is being crossed; and
      vii. a position and a size of the molten zone (5) are evaluated.

2. A method according to claim 1, wherein the minimum threshold value ($W_{min}$) is determined from a reference region (R) of the heat flow dynamics (W) of the image background (H).

3. A method according to claim 1, wherein the maximum threshold value ($W_{max}$) is determined from a test region (T),
   with the test region (T) being located in the center of a region (S) which represents the values of the heat flow dynamics (W) that exceed the minimum threshold value ($W_{min}$); and
   with the maximum threshold value ($W_{max}$) being an average value of the values of the heat flow dynamics (W) from the test region (T).

4. A method according to claim 1, wherein the maximum threshold value ($W_{max}$) is determined from several test regions (T) of the same size, with
   the test regions (T) being located in a region (S) which represents the values of the heat flow dynamics (W) exceeding the minimum threshold value ($W_{min}$),
   with an average value of the values of the heat flow dynamics (W) being determined for each test region (T) from the test region (T), and
   the maximum threshold value ($W_{max}$) being a maximum value of the average values.

5. A method according to claim 1, wherein the dynamic threshold value ($W_{dyn}$) is varied with an increment size ($\Delta W_{dyn}$), the increment size ($\Delta W_{dyn}$) being determined iteratively.

6. A method according to claim 1, wherein the material joint (4) is a weld point, with the molten zone (5) being referred to as weld nugget and the non-molten zone (6) being referred to as weld glue.

7. A method according to claim 6, wherein the weld point is evaluated by means of a material characteristic curve (K), with the characteristic curve (K) being determined by means of reference weld points which have different remaining material thicknesses (M) and interconnect at least two mating parts (2, 3);

the remaining material thickness (M) being measured for each reference weld point;

a peak value of a heat flow dynamics (W) being measured for each reference weld point; and the characteristic curve (K) being generated from the peak values of the heat flow dynamics (W) and the associated remaining material thicknesses (M).

8. A method according to claim 7, wherein the maximum threshold value ($W_{max}$) is compared with a first limiting value ($G_1$), with the presence of a hole in the weld point being indicated if said maximum threshold value ($W_{max}$) exceeds said limiting value ($G_1$).

9. A method according to claim 7, wherein the maximum threshold value ($W_{max}$) is compared with a second limiting value ($G_2$), with the presence of a cavity in the weld point being indicated if said maximum threshold value ($W_{max}$) is less than the second limiting value ($G_2$).

10. A method according to claim 6, wherein surface damages of the weld point are detected by means of another image, with the image being provided with a coordinate system which is identical to that of the result image by means of which the weld nugget was detected; and the detection and evaluation of surface damages taking place in the detected region ($B_i$) of the weld nugget.

* * * * *